United States Patent
Hirose et al.

(10) Patent No.: US 8,132,913 B2
(45) Date of Patent: Mar. 13, 2012

(54) ADAPTIVE OPTICS APPARATUS AND IMAGING APPARATUS INCLUDING THE SAME

(75) Inventors: Futoshi Hirose, Yokohama (JP); Kenichi Saito, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/907,826

(22) Filed: Oct. 19, 2010

(65) Prior Publication Data

US 2011/0096293 A1    Apr. 28, 2011

(30) Foreign Application Priority Data

Oct. 23, 2009 (JP) ................... 2009-244956

(51) Int. Cl.
*A61B 3/14* (2006.01)
*A61B 3/10* (2006.01)

(52) U.S. Cl. .................. 351/206; 351/208; 351/221
(58) Field of Classification Search ........... 351/200–246
See application file for complete search history.

(56) References Cited

U.S. PATENT DOCUMENTS 7,367,672 B2 * 5/2008 Akita ..................... 351/206
7,703,922 B2 * 4/2010 Van de Velde ............. 351/221

FOREIGN PATENT DOCUMENTS

JP    2007-014569 A    1/2007
WO    20030105678 A2    12/2003

OTHER PUBLICATIONS

Love et al, Polarization Insensitive 127-Segment Liquid Crystal Wavefront Corrector, pp. 288-290/AThC25/1-3, 1996, XP000874813.
Maurer et al, Tailoring of Arbitrary Optical Vector Beams, pp. 1-20, New Journal of Physics, 9, 2007, XP020122657.
Sergio R. Restaino et al., "Progress Report of USAF Research Laboratory Liquid Crystal AO Program", Proc. SPIE, vol. 3353, 776-781 Mar. 1998.

* cited by examiner

*Primary Examiner* — Mohammed Hasan
(74) *Attorney, Agent, or Firm* — Canon U.S.A., Inc., IP Division

(57) ABSTRACT

An adaptive optics apparatus includes a first conversion unit configured to convert a polarization direction of one of two polarization components of light to a polarization direction of the other of the polarization components, the light being emitted by a light source; a light modulation unit configured to modulate the two polarization components of light converted by the first conversion unit in the polarization directions that have been converted; a second conversion unit configured to convert directions of polarization components of the light modulated by the light modulation unit to directions that intersect with each other; and an irradiation unit configured to irradiate the object with the light that is converted by the light modulation unit.

11 Claims, 8 Drawing Sheets

100

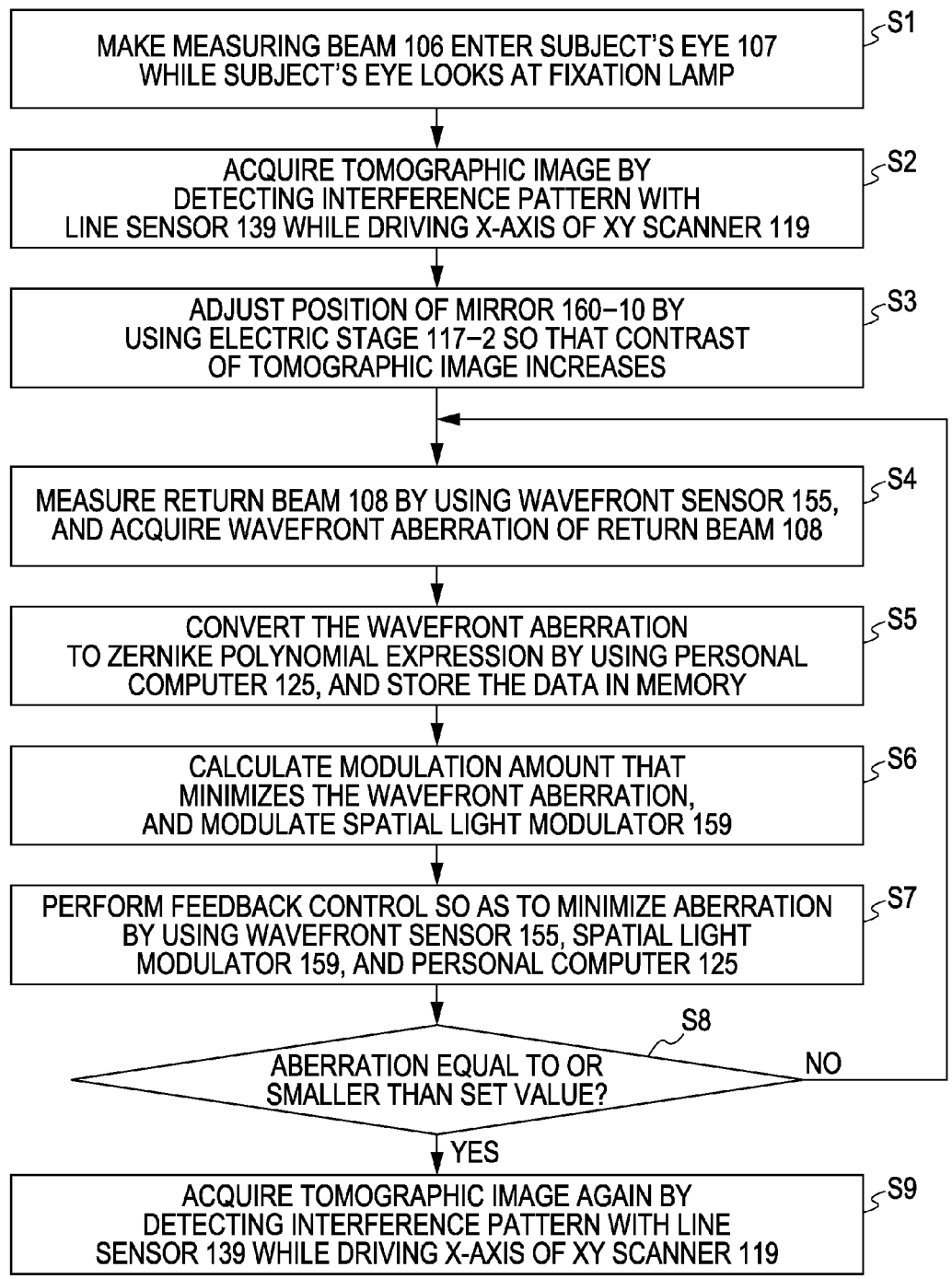

ADAPTIVE OPTICS APPARATUS AND IMAGING APPARATUS INCLUDING THE SAME

BACKGROUND OF THE INVENTION

1. Field of the Invention

The present invention relates to an adaptive optics apparatus and an imaging apparatus including the adaptive optics apparatus. In particular, the present invention relates to an optical imaging apparatus and an optical imaging method used for ophthalmologic diagnosis and the like.

2. Description of the Related Art

Optical coherence tomography (OCT) using multi-wavelength optical interference is a method of acquiring a high resolution tomographic image of a subject (in particular, an eye ground). Hereinafter, an optical tomographic imaging apparatus that acquires an optical tomographic image by using OCT will be referred to as an OCT apparatus. In recent years, it has become possible to acquire a high-horizontal-resolution tomographic image of a retina by increasing the diameter of the measuring beam used in a Fourier domain OCT apparatus. On the other hand, the increased diameter of the beam diameter of the measuring beam has caused a problem in that, when acquiring a tomographic image of a retina, the signal to noise ratio and the resolution of the tomographic image is decreased due to the aberration generated by the distortion of a curved surface and unevenness of the index of refraction of a subject's eye. To address the problem, an adaptive optics OCT apparatus including an adaptive optics system has been developed. The adaptive optics system measures the aberration of a subject's eye using a wavefront sensor in real time and corrects the aberration using a wavefront correction device, so that a high-horizontal-resolution tomographic image can be acquired.

Japanese Patent Laid-Open No. 2007-14569 describes an ophthalmologic imaging apparatus including such an adaptive optics system. The apparatus is a scanning laser ophthalmoscope (SLO apparatus) that acquires an image of an eye ground by using an adaptive optics system, a liquid crystal spatial phase modulator, a polygon mirror, a galvano mirror, and other components. This ophthalmologic imaging apparatus corrects the aberration generated in a subject's eye by using the liquid crystal spatial phase modulator, thereby preventing the horizontal resolution from decreasing. In general, a liquid crystal spatial phase modulator modulates a specific polarization component aligned with the orientation of liquid crystal and does not modulate other polarization components. Therefore, it is difficult for the ophthalmologic imaging apparatus to correct a polarization component irrespective of the polarization state of reflected light reflected from the eye ground. In this respect, the ophthalmologic imaging apparatus has a room for improvement in acquiring a high-horizontal-resolution image. Regarding a spatial phase modulator for use in an adaptive optics system, "Progress report of USAF Research Laboratory liquid crystal AO program", Proc. SPIE, Vol. 3353, 776 (1998) describes a transmissive liquid crystal spatial phase modulator in which two liquid crystal elements having different liquid-crystal orientations are stacked. This spatial phase modulator can modulate an incident beam irrespective of the polarization state of the incident beam.

SUMMARY OF THE INVENTION

However, the modulator described in "Progress report of USAF Research Laboratory liquid crystal AO program", Proc. SPIE, Vol. 3353, 776 (1998), which includes two liquid crystal elements, is not cost-efficient. Moreover, the structure in which two liquid crystal elements are stacked has a problem in that it is difficult to disposed the two liquid crystal elements so as to be optically conjugate to each other. As a result, the modulator imposes a limitation on the optical design of an adaptive optics OCT apparatus. That is, it is necessary to design an optical system so that the two liquid crystal element are disposed so as to be optically conjugate to each other with respect to two polarized beams even if the liquid crystal device surfaces are deviated. As a result, the optical system tend to become complex and large.

The present invention provides an optical imaging apparatus and an optical imaging method that, by using an adaptive optics system including a spatial light modulation unit, can modulate at least one of a measuring beam and a return beam irrespective of the polarization state and can increase the signal to noise ratio of an optical image by correcting the aberration.

According to an aspect of the present invention, An adaptive optics apparatus includes a first conversion unit configured to convert a polarization direction of one of two polarization components of light to a polarization direction of the other of the polarization components, the light being emitted by a light source; a light modulation unit configured to modulate the two polarization components of light converted by the first conversion unit in the polarization directions that have been converted; a second conversion unit configured to convert directions of polarization components of the light modulated by the light modulation unit to directions that intersect with each other; and an irradiation unit configured to irradiate an object with the light that is converted by the light modulation unit.

According to the present invention, an optical imaging apparatus and an optical imaging method that, by using an adaptive optics system including a spatial light modulation unit, can modulate at least one of a measuring beam and a return beam irrespective of the polarization state and can increase the signal to noise ratio of an optical image by correcting the aberration can be realized.

Further features of the present invention will become apparent from the following description of exemplary embodiments with reference to the attached drawings.

BRIEF DESCRIPTION OF THE DRAWINGS

FIG. 3 is a flowchart illustrating steps of acquiring a tomographic image by using the OCT apparatus according to the first embodiment of the present invention.

DESCRIPTION OF THE EMBODIMENTS

Hereinafter, embodiments of the present invention will be described with reference to the drawings. Here, an optical imaging apparatus that is an OCT apparatus that acquires an image of a subject's eye will be described. However, the present invention can be applied to other optical imaging apparatuses such as a scanning laser ophthalmoscope (SLO apparatus).

First Embodiment

An OCT apparatus (optical tomographic imaging apparatus) according to a first embodiment of the present invention will be described. In particular, in the first embodiment, an OCT apparatus including an adaptive optics system that acquires a tomographic image (OCT image) of a subject's eye with high horizontal resolution will be described. The first embodiment is a Fourier domain OCT apparatus that corrects the aberration of the subject's eye by using a reflective spatial light modulator and acquires a tomographic image of a subject's eye. Such an OCT apparatus can acquire a good tomographic image irrespective of the diopter or the aberration the subject's eye. The measuring beam is split into two polarization components, and each of the polarization components enters a reflective spatial light modulator. The adaptive optics apparatus according to the present invention is not limited to the present embodiment. It is sufficient that the adaptive optics apparatus is configured so that the light modulation unit is irradiated with light in which p-polarized light and s-polarized light have the same direction. Thus, the p-polarized light and the s-polarized light can be modulated at pupil-conjugate positions, and aberration of the incident beam generated by the object can be corrected.

Moreover, aberration generated in the return beam from the object can be corrected using the same optical system. This is because, for example, if the object is a subject's eye, aberration is generated when light that has been reflected and/or scattered by the eye ground passes through the anterior ocular segment of the subject's eye again. At this time, the return beam may pass through the same optical path as the incident beam. Thus, a common light modulation unit can be used, whereby the number of components and the cost can be reduced. Here, the spatial light modulator is a reflective liquid crystal spatial phase modulator that employs the orientation of liquid crystal. As long as the spatial light modulator can modulate the phase of light, materials other than liquid crystal may be used.

Figure 1A:
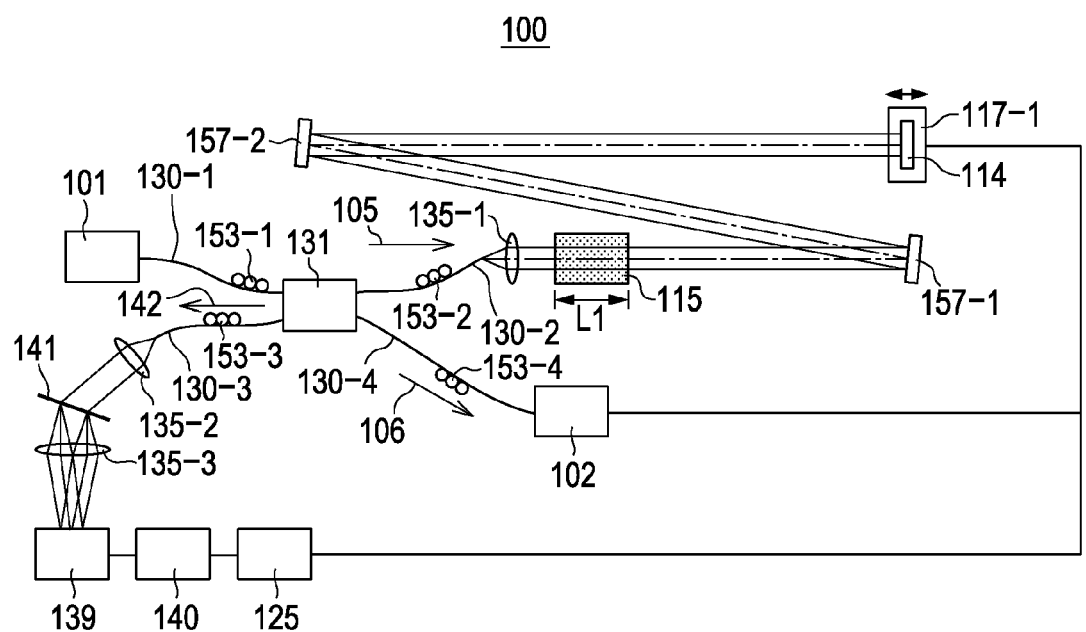
FIGS. 1A to 1C illustrate the overall structure of an OCT apparatus according to a first embodiment of the present invention.
Figure 1B:
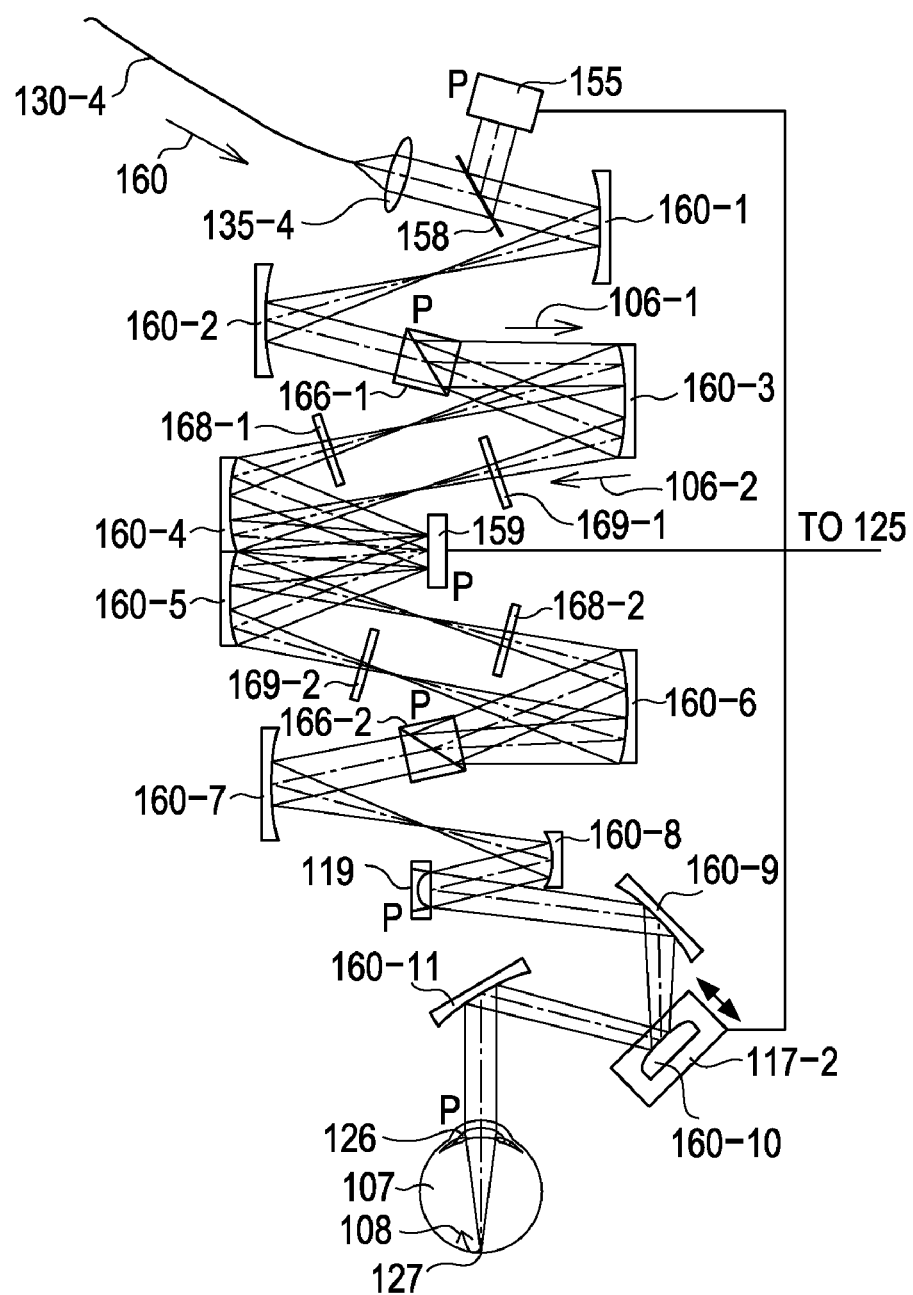

Referring to FIG. 1A, the overall structure of the OCT apparatus according to the first embodiment will be described. As illustrated in FIG. 1A, the entirety of an OCT apparatus 100 according to the first embodiment is a Michelson interferometer system. In FIG. 1A, a beam is emitted by a light source 101, and the beam travels through an optical fiber 130-1 and an optical coupler 131, where the beam is split into a reference beam 105 and a measuring beam 106 with a ratio of 90:10. The measuring beam 106 travels through a single-mode fiber 130-4 to a measuring optical path 102. FIG. 1B illustrates the structure of the measuring optical path 102. The measuring beam 106 travels through a first Wollaston prism 166-1, a spatial light modulator 159, an XY scanner 119, spherical mirrors 160-1 to 160-11 to a subject's eye 107, which is an object to be observed. The measuring beam 106 is split into two polarization components by the first Wollaston prism 166-1. The polarization components enter the spatial light modulator 159 and combined by the second Wollaston prism 166-2 into one beam.

The measuring beam 106 is reflected or scattered by the subject's eye 107, which is an object to be observed, and returned as a return beam 108. The return beam 108 is combined with the reference beam 105 by the optical coupler 131. Polarization controllers 153-1 to 153-4 adjust the polarization states of the measuring beam 106 and the reference beam 105.

The reference beam 105 and the return beam 108 are combined and then split into wavelength components by a transmissive grating 141 and enter a line sensor 139. The line sensor 139 converts the intensity of light at each position (wavelength) to a voltage signal, and a tomographic image of the subject's eye 107 is formed by using the voltage signal. The aberration of the return beam 108 is measured by a wavefront sensor 155. In the first embodiment, the spatial light modulator 159 is controlled so as to reduce the aberration and so as to obtain a good tomographic image irrespective of the diopter or the aberration of the subject's eye.

Next, the light source 101 will be described. The light source 101 is a super luminescent diode (SLD), which is a typical low-coherence light source, having a wavelength of 830 nm and a bandwidth of 50 nm. The bandwidth is an important parameter that affects the resolution of an acquired tomographic image in the optical axis direction. Here, the light source is the SLD. However, other light sources, such as an amplified spontaneous emission (ASE) device or the like can be used, as long as low-coherence light can be emitted. Using near infrared light is appropriate for measuring an eye. A shorter wavelength is more appropriate, because the wavelength affects the horizontal resolution of an acquired tomographic image. In the first embodiment, the wavelength is 830 nm. The wavelength may be different from this in accordance with the position of the object to be measured.

Next, the optical path of the reference beam 105 will be described. The reference beam 105, which has been split by the optical coupler 131, travels through a single-mode fiber 130-2 to a lens 135-1 that collimates the reference beam 105 into a collimated beam having a diameter of 3 mm. Next, the reference beam 105 is reflected by the mirrors 157-1 and 157-2 to a mirror 114, which is a reference mirror. The optical path length of the reference beam 105 is made substantially the same as the optical path length of the measuring beam 106, so that the reference beam 105 can interfere with the measuring beam 106. Next, the reference beam 105 is reflected by the mirror 114, and guided again to the optical coupler 131. The reference beam 105 passes through a dispersion compensation glass 115 that compensates the reference beam 105 for the dispersion that is generated while the measuring beam 106 travels to and returns from the subject's eye 107. The dispersion compensation glass 115 has a length L1. Here, L1=23 mm, which corresponds to the diameter of an eyeball of an average Japanese person. An electric stage 117-1 can move in a direction indicated by an arrow so as to adjust the optical path length of the reference beam 105. The electric stage 117-1 is driven under the control of a personal computer 125.

Next, referring to FIG. 1B, the optical path of the measuring beam 106, which characterizes the first embodiment, will be described. The measuring beam 106, which has been split by the optical coupler 131, is guided through the single-mode fiber 130-4 to a lens 135-4 that collimates the measuring beam 106 into a collimated beam having a diameter of 3 mm. The polarization controller 153-4 can adjust the polarization state of the measuring beam 106. Here, the polarization state of the measuring beam 106 can be circular polarized. The measuring beam 106 passes through a beam splitter 158, is reflected by the spherical mirrors 160-1 and 160-2, and enters the first Wollaston prism (first polarizing beam splitter) 166-1. Here, the measuring beam 106 is split into a first measuring beam (first optical path) 106-1 that is an s-polarization component (perpendicular to the paper surface) and a second measuring beam (second optical path) 106-2 that is a p-polarization component (parallel to the paper surface). The angle between the measuring beams 106-1 and 106-2 is 10°.

The first measuring beam 106-1 is reflected by the spherical mirror 160-3 and enters a half-wave plate 168-1, which is a first polarization adjustment unit, so that the polarization is rotated by 90° and the first measuring beam 106-1 becomes a linearly polarized beam that is parallel to the paper surface. Then, the first measuring beam 106-1 is guided to the spherical mirror 160-4. The second measuring beam 106-2 is reflected by the spherical mirror 160-3 and travels through an optical path compensating plate (first compensating plate) 169-1 to the spherical mirror 160-4. The first measuring beam 106-1, which is one of the polarization components, and the second measuring beam 106-2, which is the other of the polarization components, is reflected by the spherical mirror 160-4, enter the spatial light modulator 159 at the same position, and are modulated. The spatial light modulator 159 is oriented so as to modulate the phase of p-polarized light (parallel to the paper surface). Next, the first measuring beam 106-1 is reflected by the spherical mirror 160-5, and travels through an optical path compensating plate (second compensating plate) 169-2 to the spherical mirror 160-6. The second measuring beam 106-2 is reflected by the spherical mirror 160-5 and enters a half-wave plate (second half-wave plate) 168-2, which is a second polarization adjustment unit, so that the polarization is rotated by 90° and the second measuring beam 106-2 becomes a linearly polarized beam that is perpendicular to the paper surface. Then, the second measuring beam 106-2 is guided to the spherical mirror 160-6.

The first measuring beam 106-1 and the second measuring beam 106-2 are reflected by the spherical mirror 160-6, and enter the beam splitting surface of the second Wollaston prism (second polarizing beam splitter) 166-2 at the same position, which is disposed nearer to the object than the first Wollaston prism. The first and second measuring beams 106-1 and 106-2 are combined to become the measuring beam 106 again. The optical path compensating plates 169-1 and 169-2 respectively compensate the half-wave plates 168-1 and 168-2 for the optical path length or the deviation. The spatial light modulator 159 modulates a polarization component having a specific polarization direction by employing the orientation of liquid crystal. Therefore, as described above, the measuring beam 106 is split into the first measuring beam 106-1 and the second measuring beam 106-2 having different polarization. Moreover, the polarization direction of first measuring beam 106-1 is rotated by 90° so that the polarization directions of the measuring beams 106-1 and 106-2 become the same, whereby the measuring beam 106 can be modulated irrespective of the polarization state of the measuring beam 106.

Here, the horizontal magnification of the spatial light modulator 159 with respect to the first Wollaston prism 166-1 is 2, and the beam diameter of each of the measuring beams 106-1 and 106-2 is 6 mm when the measuring beams 106-1 and 106-2 enter the spatial light modulator 159. The angle between the measuring beams 106-1 and 106-2 is 5°. Likewise, the horizontal magnification of the spatial light modulator 159 with respect to the second Wollaston prism 166-2 is 2. As described above, the polarization directions of the measuring beam 106-1 and 106-2 can be perpendicular to each other. However, in practice, the polarization directions may not be perpendicular as long as they are different from each other.

Next, the measuring beam 106 is reflected by the spherical mirrors 160-7 and 160-8, and impinges on a mirror of the XY scanner 119. For simplicity, the XY scanner 119 is illustrated as a mirror. In practice, however, an X-scanning mirror and a Y-scanning mirror may be disposed adjacent to each other so as to raster scan a retina 127 in a direction perpendicular to the optical axis. The center of the measuring beam 106 is aligned with the center of the rotation center of the mirror of the XY scanner 119. The spherical mirrors 160-9 to 160-11, which serve as an optical system for scanning the retina 127, make the measuring beam 106 scan the retina 127 with a point near a cornea 126 as a fulcrum. Here, the diameter of the measuring beam 106 that enters the cornea is 4 mm. In order to acquire a tomographic image having a higher horizontal resolution, the beam diameter may be larger. An electric stage 117-2 can move in a direction indicated by an arrow so as to adjust the position of a spherical mirror 160-10 attached thereto under the control of the personal computer 125. By adjusting the position of the spherical mirror 160-10, the measuring beam 106 can be focused on a predetermined layer of the retina 127 of the subject's eye 107 so as to observe the layer. Even when the subject's eye 107 has ametropia, the subject's eye can be observed. After entering the subject's eye 107, the measuring beam 106 is reflected or scattered by the retina 127 to become the return beam 108, is guided again to the optical coupler 131, and reaches the line sensor 139. The return beam 108 is split by the second Wollaston prism 166-2 into s-polarized light and p-polarized light that respectively travel along the third optical path and the fourth optical path, are modulated by the spatial light modulator 159, and combined by the first Wollaston prism 166-1.

A part of the return beam 108, which is split from the return beam 108 by the beam splitter 158, enters the wavefront sensor 155, which measures the aberration of the return beam 108. The wavefront sensor 155 is electrically connected to the personal computer 125. Here, the spherical mirrors 160-1 to 160-9 are disposed so that the cornea 126, the XY scanner 119, the wavefront sensor 155, the spatial light modulator 159, and the beam splitting surfaces of the Wollaston prisms 166-1 and 166-2 are optically conjugate to each other. The positions that are conjugate to each other are denoted by "P". Therefore, the wavefront sensor 155 can measure the aberration of the subject's eye 107. Moreover, the spatial light modulator 159 can correct the aberration of the subject's eye 107 and can recombine the polarized beams that have been split. Furthermore, the spatial light modulator 159 is controlled in real time on the basis of the aberration obtained, so that the aberration generated in the subject's eye 107 is corrected and a tomographic image having a higher horizontal resolution can be acquired. Due to the characteristics of the Wollaston prism 166, the first measuring beam 106-1 and the second measuring beam 106-2 have different beam diameters after being split. Therefore, the spherical mirrors 160-3 to 160-6 are configured so that the beam diameters of the first and the second measuring beams become the same on the spatial light modulator 159.

Instead of the spherical mirrors 160-1 to 160-11 used here, aspherical mirrors or free-form surface mirrors may be used. Here, each of the spherical mirrors 160-3 to 160-6 reflects the first measuring beam 106-1 and the second measuring beam 106-2. However, two sets of lenses may be provided so as to respectively reflect the two measuring beams. Here, the measuring beam 106 is split into polarization components by using the Wollaston prisms 166-1 and 166-2. However, other elements may be used as long as they can split a beam into polarization components. For example, a polarizing beam splitter, a Nicol prism, a Savart plate, or the like can be used. Here, the polarization direction of the measuring beam 106 is rotated by using the half-wave plates 168-1 and 168-2. However, other elements may be used as long as they can rotate the polarization direction. Instead of the spherical mirror 160-8 used here, a cylindrical mirror may be used depending on the aberration (ametropia) of the subject's eye 107. An additional lens may be disposed on the optical path of the measuring beam 106. Here, the wavefront sensor 155 measures the aberration by using the measuring beam 106. However, the aberration may be measured by using an aberration measuring beam that is emitted by another light source. An additional optical path may be made in order to measure the aberration. For example, a beam splitter may be disposed between the spherical mirror 160-11 and the cornea 126 so as to generate a beam for measuring the aberration.

Figure 1C:
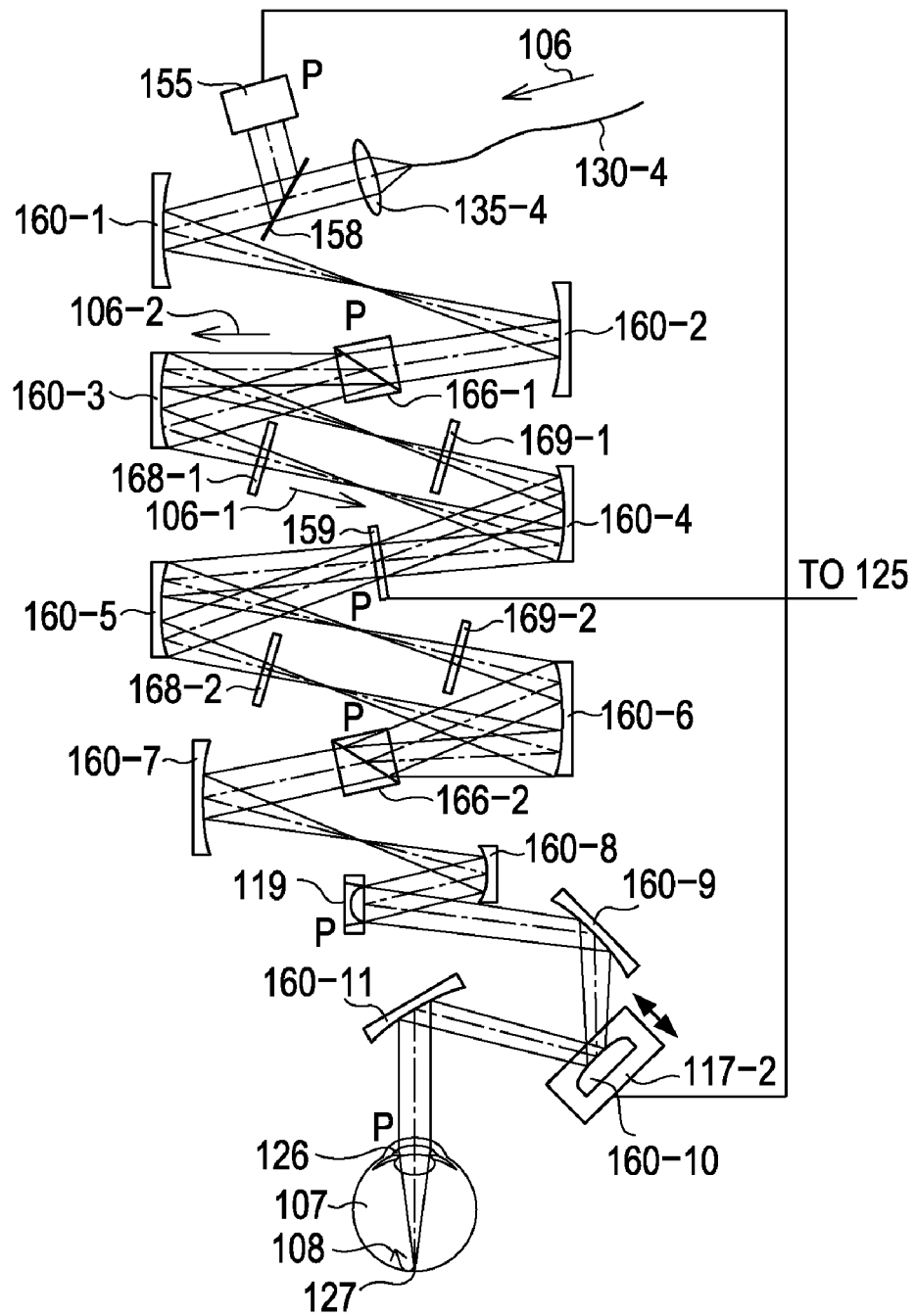

Here, after the measuring beam 106 is reflected by the spherical mirror 160-1, the measuring beam 106 is split by the Wollaston prism 166-1 into the first measuring beam 106-1 that is s-polarized and the second measuring beam 106-2 that is p-polarized. However, the measuring beam 106 may be split at another position so as to make a measuring optical path. Here, a reflective liquid-crystal spatial light modulator is used as the spatial light modulator 159. However, a transmissive spatial light modulator may be used. For example, as illustrated in FIG. 1C, a transmissive liquid-crystal spatial phase modulator can be used as the spatial light modulator 159. Because the structure is the same as that of FIG. 1B except for the type of the spatial light modulator 159, the same components are denoted by the same numerals and redundant description will be omitted.

Next, the structure of the measurement system of the OCT apparatus according to the first embodiment will be described. The OCT apparatus 100 can acquire a tomographic image (OCT image) that is formed of the intensity of an interference signal measured by a Michelson interferometer system. In the measurement system, the return beam 108, which has been reflected or scattered by the retina 127, is combined with the reference beam 105 by the optical coupler 131 to generate a combined beam 142. The combined beam 142 travels through an optical fiber 130-3 and a lens 135-2 and enters the transmissive grating 141. The combined beam 142 is split into wavelength components by the transmissive grating 141, focused by a lens 135-3, and the line sensor 139 converts the intensity of the combined beam at each position (wavelength) to a voltage. To be specific, an interference pattern of spectral regions on the wavelength axis is observed on the line sensor 139. The voltage signals that have been acquired by the line sensor 139 are converted to digital data by a frame grabber 140. The personal computer 125 performs data processing and generates a tomographic image.

Here, the line sensor 139 has 1024 pixels and can acquire the intensity of each of the wavelengths (1024 wavelength segments) of the combined beam 142. A part of the return beam 108, which is split by the beam splitter 158, enters the wavefront sensor 155, and the aberration of the return beam 108 is measured. The wavefront sensor 155 is a Shack-Hartmann wavefront sensor. The aberration is represented by using a Zernike polynomial, which represents the aberration of the subject's eye 107. The Zernike polynomial includes tilt terms, defocus terms, astigmatism terms, coma terms, trefoil terms, etc.

Figure 2A:
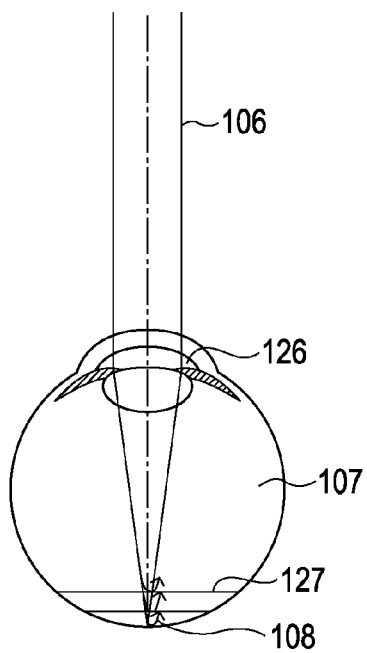
FIGS. 2A to 2C illustrate a method of acquiring a tomographic image by using the OCT apparatus according to the first embodiment of the present invention.
Figure 2B:
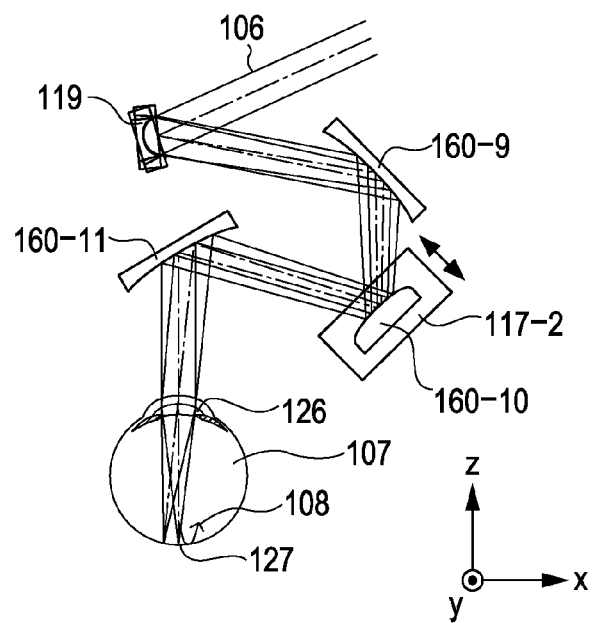
Figure 2C:
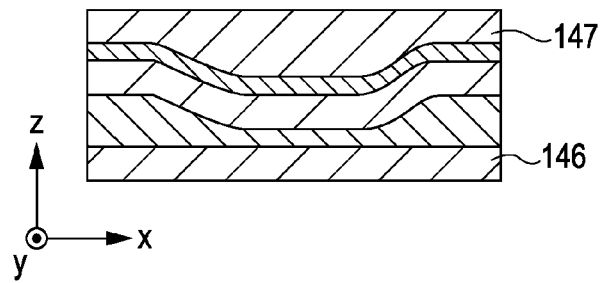

Next, a method of acquiring a tomographic image by using the OCT apparatus will be described. The OCT apparatus 100 can acquire a tomographic image of the retina 127 by controlling the XY scanner 119 and acquiring an interference pattern with the line sensor 139 (FIGS. 1A to 1C). Referring to FIGS. 2A to 2C, a method of acquiring a tomographic image (in a plane parallel to the optical axis) of the retina 127 will be described. FIG. 2A is a schematic view of the subject's eye 107, which is being observed by the OCT apparatus 100. As illustrated in FIG. 2A, the measuring beam 106 passes through the cornea 126 and enters the retina 127. In the retina 127, the measuring beam 106 is reflected and scattered at various positions and becomes the return beam 108. The return beam 108, which has been delayed at the various positions, reaches the line sensor 139. Here, the light source 101 has a wide bandwidth and a short coherence length. Therefore, the line sensor 139 can detect an interference pattern in the case where the optical path length of the reference optical path is substantially equal to the optical path length of the measuring optical path. As described above, the line sensor 139 acquires an interference pattern of spectral regions on the wavelength axis. Next, the interference pattern, which is the information along the wavelength axis, is converted to an interference pattern on an optical frequency axis with consideration of the characteristics of the line sensor 139 and the transmissive grating 141. The interference pattern on the optical frequency axis is inverse Fourier transformed to acquire the information in the depth direction.

As illustrated in FIG. 2B, by detecting the interference pattern while driving the X-axis of the XY scanner 119, the interference pattern for each position on the X-axis is acquired, i.e., the information in the depth direction for each position on the X-axis can be acquired. As a result, a two-dimensional distribution of the intensity of the return beam 108 in the XZ-plane, which is a tomographic image 132 (FIG. 2C), is acquired. In practice, the tomographic image 132 is the arrayed intensities of the return beam 108, and displayed, for example, by representing the intensities in gray scale. Here, only the boundaries of the acquired tomographic image are illustrated. A pigmented layer 146 and an optic nerve fiber layer 147 of the retina are illustrated.

Referring to FIGS. 1A to 3, the steps of acquiring a tomographic image by using the OCT apparatus will be described. FIG. 3 is a flowchart illustrating the steps of acquiring a tomographic image by using the OCT apparatus 100. FIG. 3 illustrates the steps of correcting an aberration generated in the subject's eye 107 having myopia and astigmatism by using the spatial light modulator 159 so as to acquire a high-horizontal-resolution tomographic image of the retina 127. Needless to say, the same method can be used in the case where the subject's eye 107 has only myopia or hyperopia. The tomographic image is acquired by performing the following steps (1) to (9). The steps may be performed sequentially or in a different order. The steps may be automatically performed by using a computer.

FIG. 3 is a flowchart of the process of acquiring the tomographic image.

(1) In step 1 (S1 in FIG. 3), the measuring beam 106 is made to enter the subject's eye 107 while the subject's eye 107 looks at a fixation lamp (not shown). Here, the position of the spherical mirror 160-10 is adjusted by the electric stage 117-2 so that the measuring beam 106 enters the subject's eye 107 as a collimated beam.

(2) In step 2 (S2 in FIG. 3), a tomographic image (not shown) is acquired by detecting an interference pattern with the line sensor 139 while driving the X-axis of the XY scanner 119.

(3) In step 3 (S3 in FIG. 3), while performing step 2, the position of the spherical mirror 160-10 is adjusted by using the electric stage 117-2 so that the contrast of the tomographic image increases.

(4) In step 4 (S4 in FIG. 3), the return beam 108 is measured by using the wavefront sensor 155, and the aberration of the return beam 108 is acquired.

(5) In step 5 (S5 in FIG. 3), the acquired aberration is converted to a Zernike polynomial expression by using the personal computer 125, and the data is stored in a memory of the personal computer 125.

(6) In step 6 (S6 in FIG. 3), a modulation amount that minimizes the acquired aberration is calculated, and the spatial light modulator 159 is modulated.

(7) In step 7 (S7 in FIG. 3), feedback control is performed so as to minimize aberration by using the wavefront sensor 155, the spatial light modulator 159, and the personal computer 125 so as to control the spatial light modulator 159 in real time.

(8) In step 8 (S8 in FIG. 3), whether the aberration is equal to or smaller than a set value is determined, and steps 4 to 7 are repeated until the aberration converges. The set value can be about 0.1 μm (root mean square (RMS)).

(9) In step 9 (S9 in FIG. 3), while driving the X-axis of the XY scanner 119, the interference pattern is detected by using the line sensor 139, and a tomographic image is obtained again.

As described above, with the structure according to the first embodiment, the measuring beam or the return beam can be modulated by using one spatial light modulator and the aberration can be corrected irrespective of the polarization state. As a result, the signal to noise ratio of a tomographic image can be increased. The aberration of at least one of the measuring beam and the return beam is corrected on the basis of the aberration, so that the aberration of the object (here, the subject's eye) can be corrected, and thereby the resolution and the signal to noise ratio of the tomographic image can be increased. The spatial light modulator and the wavefront sensor are disposed optically conjugate to each other, so that the aberration can be efficiently corrected. The first Wollaston prism, the second Wollaston prism, and the spatial light modulator are optically conjugate to each other, so that the first measuring beam and the second measuring beam can be easily recombined. The horizontal magnification of the spatial light modulator with respect to at least one of the first Wollaston prism and the second Wollaston prism is larger than 1, so that the angle between the first measuring beam and the second measuring beam can be easily reduced. Therefore, the effect of the angular dependence of the spatial light modulator can be minimized. The half-wave plates are each disposed on the optical path of the first measuring beam and on the optical path of the second measuring beam, so that the direction of the polarization of the first measuring beam and the second measuring beam can be rotated. Thus, each of the first measuring beam and the second measuring beam can be made to enter the spatial light modulator with a desired polarization state, so that the efficiency of modulation can be increased. Moreover, each of the first measuring beam and the second measuring beam can be made to enter the half-wave plate in a desired polarization state, so that the first measuring beam and the second measuring beam can be recombined.

The half-wave plates are each disposed on the optical path of the first measuring beam between the first Wollaston prism and the spatial light modulator and on the optical path of the second measuring beam between the second Wollaston prism and the spatial light modulator, so that the optical paths can be simply made. The optical path compensating plates are each disposed on the optical path of the first measuring beam between the second Wollaston prism and the spatial light modulator and on the optical path of the second measuring beam between the first Wollaston prism and the spatial light modulator. Thus, the optical path length or the deviation of the optical path of the first measuring beam and the optical path of the second measuring beam can be compensated, so that decrease of the resolution due to the branching of the measuring optical path can be prevented. The optical path can be made by replacing at least one of the first Wollaston prism and the second Wollaston prism with a general polarizing beam splitter. The optical path can be simply made by using the Wollaston prism as the polarizing beam splitter. The optical path can be made by replacing at least one of the first Wollaston prism and the second Wollaston prism with a Nicol prism or a Savart plate. A beam from the light source is split into the measuring beam and the reference beam, and the return beam, which is generated by irradiating the object with the measuring beam, and the reference beam, which has traveled through the reference optical path, are made to interfere with each other, and the tomographic image is acquired by using the intensity of the interference signal due to the interference. Thus, a tomographic image having a high signal to noise ratio can be acquired irrespective of the polarization state of the measuring beam or the return beam.

Moreover, according to the first embodiment, light emitted from the light source is split into the measuring beam and the reference beam, and by using the interfere signal generated by interference between the return beam of the measuring beam with which the object is irradiated and the reference beam, which has traveled through the reference optical path, an optical imaging method of acquiring a tomographic image of the object can be constructed. In the first step, the aberration of an object is measured by using an aberration measuring unit configured to measure the aberration of the return beam generated in the object. The aberration measuring unit is disposed on the optical path from the light source to the object together with one spatial light modulation unit employing the orientation of liquid crystal. The spatial light modulation unit modulates at least one of the measuring beam and the return beam irrespective of the polarization state of the measuring beam or the return beam by making different polarization components that have been split from the measuring beam or the return beam enter and exit through the polarization adjustment unit. In the second step, the modulation amount for the spatial light modulation unit is calculated to correct the aberration on the basis of the measurement result obtained by the aberration measuring unit. The modulation amount of the spatial light modulation unit is controlled by using a control unit that controls the modulation amount of the spatial light modulation unit on the basis of the modulation amount that has been calculated. Thus, the measuring beam or the return beam can be modulated and the aberration can be corrected irrespective of the polarization state. As a result, the signal to noise ratio of the tomographic image can be increased.

Second Embodiment

Next, a second embodiment will be described. In the second embodiment, an OCT apparatus including an adaptive optics system that acquires a tomographic image (OCT image) of a subject's eye with high horizontal resolution will be described. As with the first embodiment, the second embodiment is a Fourier domain OCT apparatus that corrects the aberration of the subject's eye by using the reflective spatial light modulator and acquires a tomographic image of a subject's eye. Such an OCT apparatus can acquire a good tomographic image irrespective of the diopter or the aberration the subject's eye. The measuring beam is split into two polarization components, and each of the polarization components enters a reflective spatial light modulator. In the first embodiment, the optical system is a reflective optical system using spherical mirrors as the main components. In the second embodiment, the optical system is a refractive optical system using lenses instead of the spherical mirrors.

Figure 4A:
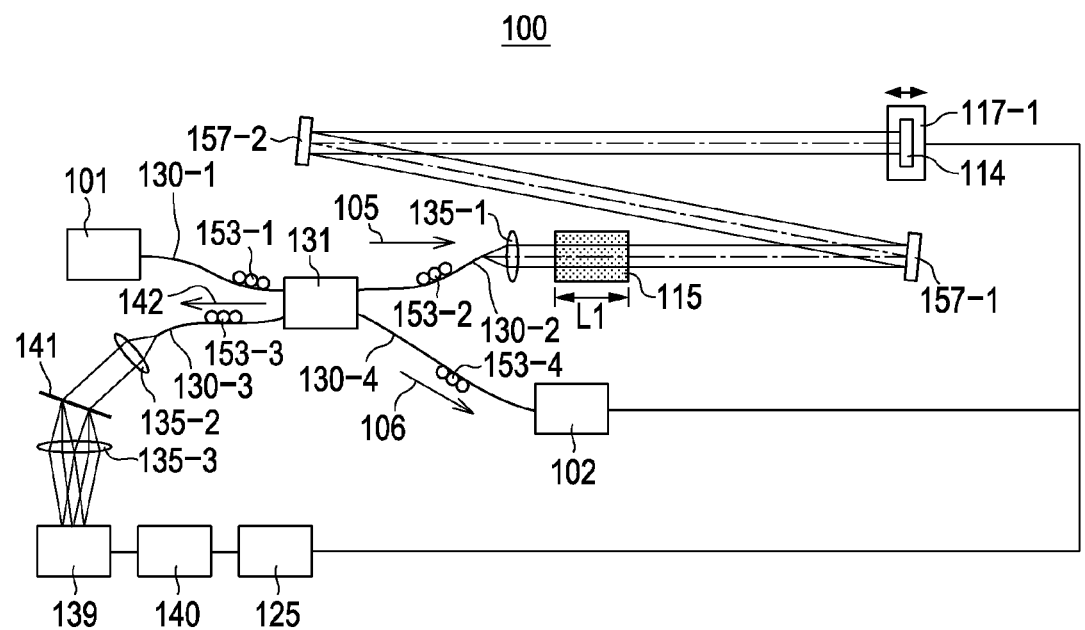
FIGS. 4A and 4B illustrate the overall structure of an OCT apparatus according to a second embodiment of the present invention.
Figure 4B:
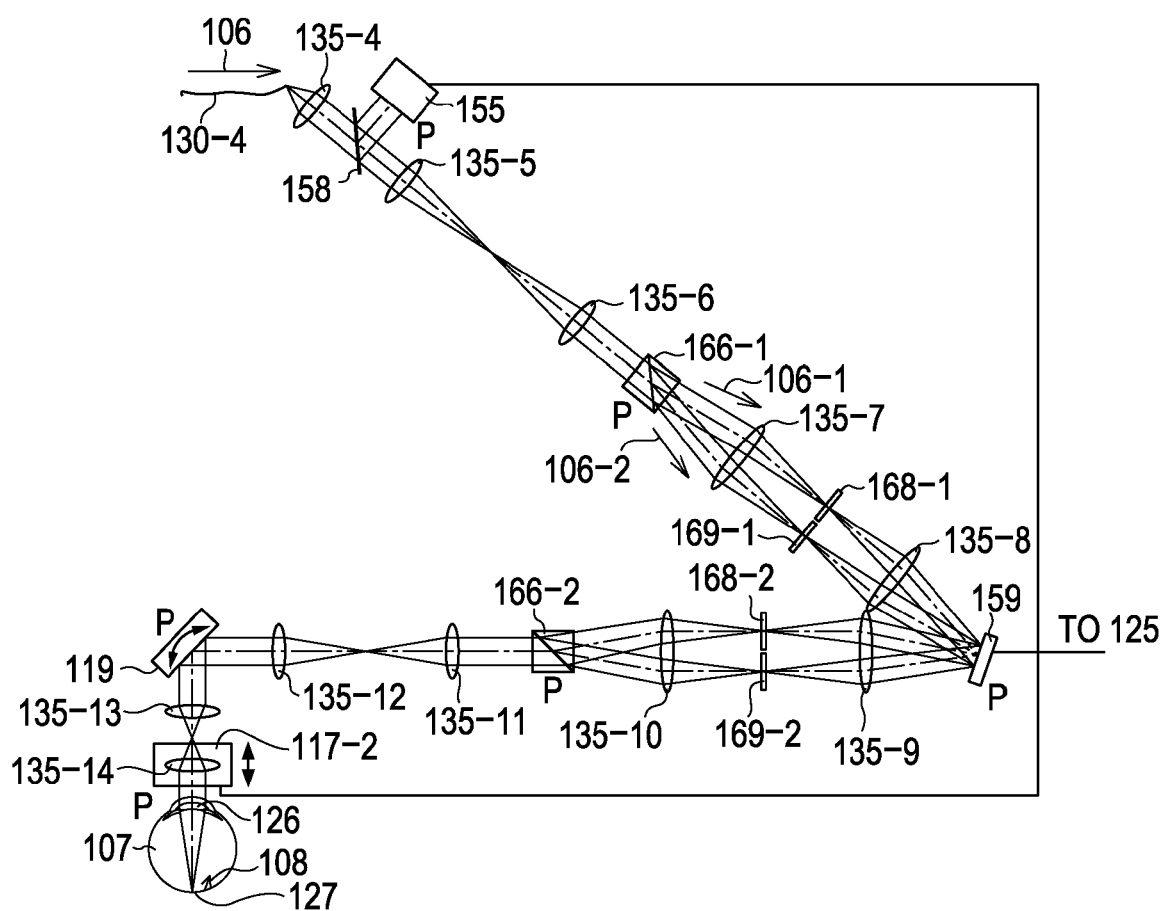

Referring to FIGS. 4A and 4B, the overall structure of the OCT apparatus according to the second embodiment will be described. In the second embodiment, the elements the same as those of FIGS. 1A to 1C are denoted by the same numerals, and redundant description will be omitted. FIG. 4B illustrates the structure of the measuring optical path 102 in FIG. 4A. In FIG. 4B, the measuring beam 106 travels through the first Wollaston prism 166-1, the spatial light modulator 159, the second Wollaston prism 166-2, the XY scanner 119, and lenses 135-4 to 135-14 to the subject's eye 107, which is an object to be observed. The measuring beam 106 is split into two polarization components by the first Wollaston prism 166-1. The polarization components enter the spatial light modulator 159 and combined by the second Wollaston prism 166-2 into one beam. The aberration of the return beam 108 is measured by the wavefront sensor 155. In the second embodiment, the spatial light modulator 159 is controlled so as to reduce the aberration and so as to obtain a good tomographic image irrespective of the diopter or the aberration of the subject's eye. In the second embodiment, a reflective spatial light modulator is used. However, a transmissive spatial light modulator may be used. The description of the light source 101 and the reference optical path, which are the same as those of the first embodiment, is omitted.

Next, referring to FIG. 4B, the optical path of the measuring beam 106, which characterizes the second embodiment, will be described. The measuring beam 106, which has been split by the optical coupler 131, is guided through the single-mode fiber 130-4 to the lens 135-4 that collimates the measuring beam 106 into a collimated beam having a diameter of 3 mm. The measuring beam 106 passes through the beam splitter 158 and the lenses 135-5 and 135-6, and enters the first Wollaston prism 166-1. Here, the measuring beam 106 is split into the first measuring beam 106-1 that is an s-polarization component (perpendicular to the paper surface) and the second measuring beam 106-2 that is a p-polarization component (parallel to the paper surface). The angle between the measuring beams 106-1 and 106-2 is 10°.

The first measuring beam 106-1 travels through the lens 135-7 and enters the half-wave plate 168-1 so that the polarization is rotated, and the first measuring beam 106-1 becomes a linearly polarized beam that is parallel to the paper surface. Then, the first measuring beam 106-1 is guided to the lens 135-8. The second measuring beam 106-2 travels through the lens 135-7 and the optical path compensating plate 169-1 to the lens 135-8. Next, the first measuring beam 106-1 and the second measuring beam 106-2 enter the spatial light modulator 159 at the same position, and are modulated by the spatial light modulator 159. The spatial light modulator 159 is oriented so as to modulate the phase of p-polarized light (parallel to the paper surface). Next, the first measuring beam 106-1 travels through the lens 135-9 and the optical path compensating plate 169-2 to the lens 135-10. The second measuring beam 106-2 travels through a lens 135-9 and enters the half-wave plate 168-2, so that the polarization is rotated and the second measuring beam 106-2 becomes a linearly polarized beam that is perpendicular to the paper surface. Then, the second measuring beam 106-2 is guided to the lens 135-10. The first measuring beam 106-1 and the second measuring beam 106-2 enter the beam splitting surface of the second Wollaston prism 166-2 at the same position. The first and second measuring beams 106-1 and 106-2 are combined to become the measuring beam 106 again. The optical path compensating plates 169-1 and 169-2 respectively compensate the half-wave plates 168-1 and 168-2 for the optical path length or the deviation.

Next, the measuring beam 106 travels through the lenses 135-11 and 135-12, and enters the mirror of the XY scanner 119. The lenses 135-13 and 135-14, which serve as an optical system for scanning the retina 127, make the measuring beam 106 scan the retina 127 with a point near the cornea 126 as a fulcrum. The electric stage 117-2 can move in a direction indicated by an arrow so as to adjust the position of the lens 135-14 attached thereto under the control of the personal computer 125. By adjusting the position of the lens 135-14, the measuring beam 106 can be focused on a predetermined layer of the retina 127 of the subject's eye 107 so as to observe the layer. Even when the subject's eye 107 has ametropia, the subject's eye can be observed. After entering the subject's eye 107, the measuring beam 106 is reflected or scattered by the retina 127 to become the return beam 108, is guided again to the optical coupler 131, and reaches the line sensor 139. The return beam 108 is split into s-polarized light and p-polarized light by the second Wollaston prism 166-2. The s-polarized light and p-polarized light are respectively modulated by the spatial light modulator 159 and combined by the first Wollaston prism 166-1. A part of the return beam 108, which is split from the return beam 108 by the beam splitter 158, enters the wavefront sensor 155, which measures the aberration of the return beam 108. The wavefront sensor 155 is electrically connected to the personal computer 125.

Here, the lenses 135-4 to 135-14 are disposed so that the cornea 126, the XY scanner 119, the wavefront sensor 155, the spatial light modulator 159, and the beam splitting surfaces of the Wollaston prisms 166-1 and 166-2 are optically conjugate to each other. The positions that are conjugate to each other are denoted by "P". Therefore, the wavefront sensor 155 can measure the aberration of the subject's eye 107. Moreover, the spatial light modulator 159 can correct the aberration of the subject's eye 107, and beams of different polarization components that have been split can be recombined. Furthermore, the spatial light modulator 159 is controlled in real time on the basis of the aberration obtained, so that the aberration generated in the subject's eye 107 is corrected and a tomographic image having a higher horizontal resolution can be acquired. Due to the characteristics of the Wollaston prisms 166-1 and 166-2, the first measuring beam 106-1 and the second measuring beam 106-2 have different beam diameters after being split. Therefore, the lenses 135-4 to 135-14 are configured so that the beam diameters of the first and the second measuring beams become the same on the spatial light modulator 159. Here, each of the lenses 135-7 to 135-10 reflects the first measuring beam 106-1 and the second measuring beam 106-2. However, two sets of lenses may be provided so as to respectively reflect the two measuring beams. Instead of a spherical lens used as the lens 135-14 here, a cylindrical lens may be used depending on the aberration (ametropia) of the subject's eye 107. An additional lens may be disposed on the optical path of the measuring beam 106. Here, after the measuring beam 106 has travelled through the lens 135-6, the measuring beam 106 is split by the Wollaston prism 166-1 into the first measuring beam 106-1 that is s-polarized and the second measuring beam 106-2 that is p-polarized. However, the measuring optical path may be configured so that the measuring beam 106 is split at another position. Here, a reflective liquid-crystal spatial phase modulator is used as the spatial light modulator 159. However, a transmissive liquid crystal spatial phase modulator may be used. The description of the structure of the measurement system and the method of acquiring a tomographic image, which are the same as those of the first embodiment, is omitted. The description of the steps of acquiring a tomographic image is omitted, because the steps are the same as those of the first embodiment, except that a predetermined layer of the retina 127 of the subject's eye 107 is observed by focusing the measuring beam 106 on the layer by adjusting the position of the lens 135-14.

Third Embodiment

Next, a third embodiment will be described. In the third embodiment, an OCT apparatus including an adaptive optics system that acquires a tomographic image (OCT image) of a subject's eye with high horizontal resolution will be described. As with the first and second embodiments, the third embodiment is a Fourier domain OCT apparatus that corrects the aberration of the subject's eye by using the reflective spatial light modulator and acquires a tomographic image of a subject's eye. Such an OCT apparatus can acquire a good tomographic image irrespective of the diopter or the aberration the subject's eye. The measuring beam is split into two polarization components, and each of the polarization components enters a reflective spatial light modulator. In the second embodiment, the measuring optical path is made by using two Wollaston prisms. In the third embodiment, one common Wollaston prism is used so that the length of the measuring optical path is reduced.

Figure 5:
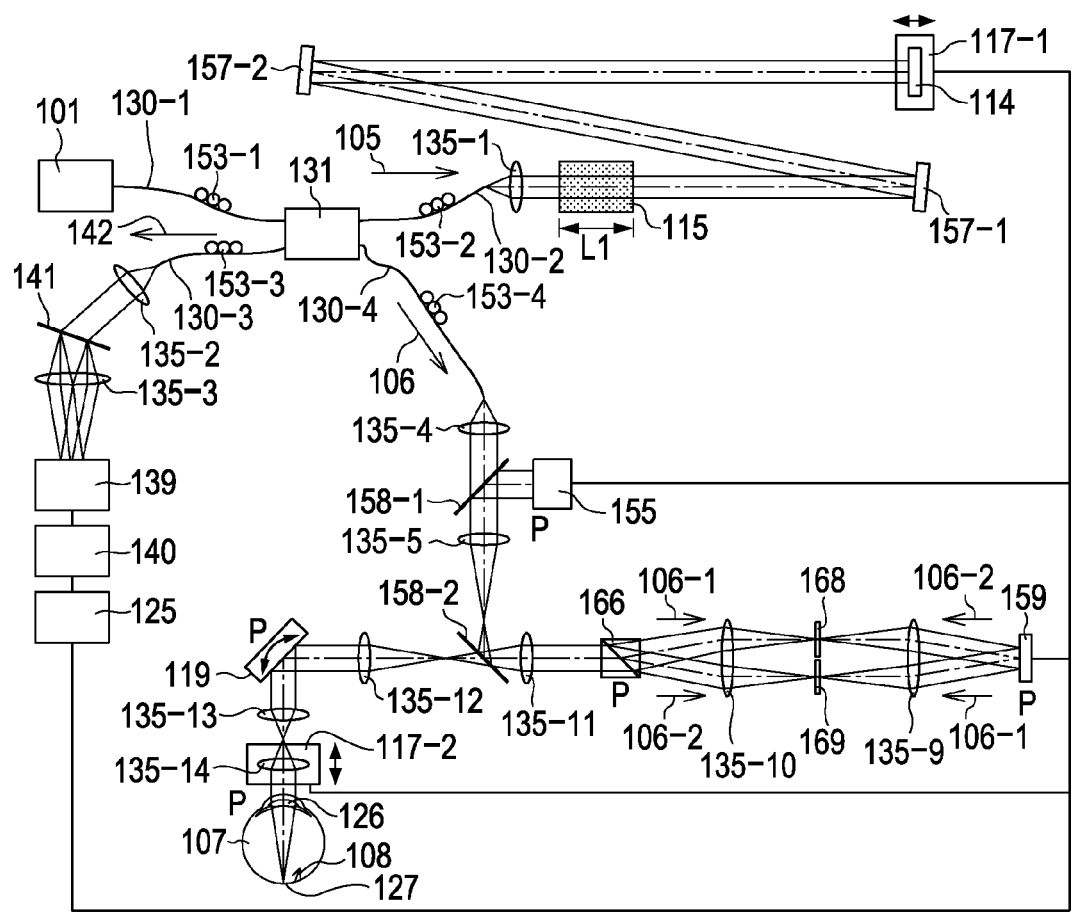
FIG. 5 illustrates the overall structure of an OCT apparatus according to a third embodiment of the present invention.

Referring to FIG. 5, the overall structure of the OCT apparatus according to the third embodiment will be described. In the third embodiment, the elements the same as those of FIGS. 4A and 4B are denoted by the same numerals, and redundant description will be omitted. The measuring beam 106 is reflected by a beam splitter 158-2, split by the Wollaston prism 166 in to two polarization components, enters the spatial light modulator 159, and is modulated by the spatial light modulator 159. The measuring beam 106 travels through the beam splitter 158-2, the XY scanner 119, the lenses 135-12 to 135-14 to the subject's eye 107, which is an object to be observed. The aberration of the return beam 108 is measured by the wavefront sensor 155. Here, the spatial light modulator 159 is controlled so as to reduce the aberration and so as to obtain a good tomographic image irrespective of the diopter or the aberration of the subject's eye. In the third embodiment, a reflective spatial light modulator is used. However, a transmissive spatial light modulator may be used. The description of the light source 101 and the reference optical path, which is the same as that of the first embodiment, is omitted.

Next, referring to FIG. 5, the optical path of the measuring beam 106, which characterizes the third embodiment, will be described. The measuring beam 106, which has been split by the optical coupler 131, is guided through the single-mode fiber 130-4 to the lens 135-4 that collimates the measuring beam 106 into a collimated beam having a diameter of 3 mm. The measuring beam 106 travels through a beam splitter 158-1 and the lens 135-5 to the beam splitter 158-2. Here, a part of the measuring beam 106 is reflected, and the part passes through the lens 135-11 and enters the Wollaston prism 166. Here, the measuring beam 106 is split into a first measuring beam 106-1 that is an s-polarization component (perpendicular to the paper surface) and a second measuring beam 106-2 that is a p-polarization component (parallel to the paper surface). The angle between the measuring beams 106-1 and 106-2 is 10°. The first measuring beam 106-1 travels through the lens 135-10 and enters the half-wave plate 168 so that the polarization is rotated, and the first measuring beam 106-1 becomes a linearly polarized beam that is parallel to the paper surface. Then, the first measuring beam 106-1 is guided to the lens 135-9. The second measuring beam 106-2 travels through the lens 135-10 and the optical path compensating plate 169 to the lens 135-9.

Next, the first measuring beam 106-1 and the second measuring beam 106-2, enter the spatial light modulator 159 at the same position, and are modulated by the spatial light modulator 159. The spatial light modulator 159 is oriented so as to modulate the phase of p-polarized light (parallel to the paper surface). Here, the horizontal magnification of the spatial light modulator 159 with respect to the Wollaston prism 166 is 2, and the beam diameter of each of the measuring beams 106-1 and 106-2 is 6 mm when the measuring beams 106-1 and 106-2 enter the spatial light modulator 159. The angle between the measuring beams 106-1 and 106-2 is 5°. Next, the first measuring beam 106-1 travels along an optical path that is different from the previous path (the lower path in FIG. 5), travels through the lenses 135-9 and 135-10 and the optical path compensating plate 169, and is guided again to the Wollaston prism 166. The second measuring beam 106-2 travels through the lens 135-9 and enters the half-wave plate 168 so that the polarization is rotated and the second measuring beam 106-2 becomes a linearly polarized beam that is perpendicular to the paper surface. The second measuring beam 106-2 travels through the lens 135-10, and is guided against to the Wollaston prism 166.

The first measuring beam 106-1 and the second measuring beam 106-2 enters the Wollaston prism 166 at the same position, and are combined to become the measuring beam 106 again. Next, the measuring beam 106 travels through the lenses 135-11 and 135-12 and enters the mirror of the XY scanner 119. The optical system, which scans the retina 127 with the measuring beam 106 by using the XY scanner 119, the lenses 135-13 and 135-14, and other components, is the same as the that of the second embodiment, and the description thereof is omitted. After entering the subject's eye 107, the measuring beam 106 is reflected or scattered by the retina 127 to become the return beam 108. The return beam 108 is split by the Wollaston prism 166 into a first return beam 108-1 that is an s-polarization component (perpendicular to the paper surface) and a second return beam 108-2 that is a p-polarization component (parallel to the paper surface). The return beams 108-1 and 108-2 respectively travel along the optical paths of the measuring beams 106-1 and 106-2, enter the spatial light modulator 159 at the same position, and are modulated by the spatial light modulator 159.

The return beams 108-1 and 108-2 reenters the Wollaston prism 166 at the same position and combined to become the return beam 108 again. A part of the return beam 108 is reflected by the beam splitter 158-2, travels through the lenses 135-4 and 135-5, is guided again to the optical coupler 131, and reaches the line sensor 139. Here, the spherical mirrors 160-1 to 160-9 are disposed so that the cornea 126, the XY scanner 119, the wavefront sensor 155, the spatial light modulator 159, and the beam splitting surfaces of the Wollaston prisms 166-1 and 166-2 are optically conjugate to each other. The positions that are conjugate to each other are denoted by "P". Therefore, the wavefront sensor 155 can measure the aberration of the subject's eye 107. Moreover, the spatial light modulator 159 can correct the aberration of the subject's eye 107 and can recombine the polarized beams that have been split. Furthermore, the spatial light modulator 159 is controlled in real time on the basis of the aberration obtained, so that the aberration generated in the subject's eye 107 is corrected and a tomographic image having a higher horizontal resolution can be acquired. Due to the characteristics of the Wollaston prism 166, the first measuring beam 106-1 and the second measuring beam 106-2 have different beam diameters after being split. Therefore, the spherical mirrors 160-3 to 160-6 are configured so that the beam diameters of the first and the second measuring beams become the same on the spatial light modulator 159.

The description of the structure of the measurement system and the method of acquiring a tomographic image, which is the same as that of the first embodiment, is omitted. The description of the steps of acquiring the tomographic image, which are the same as those of the second embodiment, is omitted. As described above, a short optical path can be made by one using one Wollaston prism for different polarized beams.

Other Embodiments

Aspects of the present invention can also be realized by a computer of a system or apparatus (or devices such as a CPU or MPU) that reads out and executes a program recorded on a memory device to perform the functions of the above-described embodiments, and by a method, the steps of which are performed by a computer of a system or apparatus by, for example, reading out and executing a program recorded on a memory device to perform the functions of the above-described embodiments. For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-244956 filed Oct. 23, 2009, which is hereby incorporated by reference herein in its entirety.

What is claimed is:

1. An adaptive optics apparatus comprising:
a first conversion unit configured to convert a polarization direction of a first of two different polarization components of light to a polarization direction of a second of the two polarization components, the light being emitted by a light source; and
a spatial light modulation unit configured to modulate the phases of the first and second polarization components of light, the first polarization component having been converted by the first conversion unit and the modulation being in the polarization direction corresponding to the polarization direction of the converted first polarization component;
a second conversion unit configured to convert the polarization direction of at least one of the first and second polarization components of the light once modulated by the light modulation unit to re-create light with polarization directions that intersect with each other; and
an irradiation unit configured to irradiate an object with the light that has intersecting polarization directions.

2. The adaptive optics apparatus according to claim 1, further comprising:
an aberration measuring unit configured to measure an aberration of the object,
wherein the spatial light modulation unit modulates light at a position that is optically conjugate to the aberration measuring unit on the basis of a measurement result obtained by the aberration measuring unit.

3. The adaptive optics apparatus according to claim 2,
wherein the object is a subject's eye,
wherein the aberration is generated in an anterior ocular segment of the subject's eye, and
wherein the spatial light modulation unit is disposed at a position that is optically conjugate to the anterior ocular segment.

4. The adaptive optics apparatus according to claim 2,
wherein light that is used by the aberration measuring unit to measure the aberration and light that is used to acquire an image of the object are emitted by light sources that are different from each other.

5. The adaptive optics apparatus according to claim 1,
wherein light returning from the object is a return beam with two polarization components, and
the second conversion unit is arranged to convert a polarization direction of a first of the two polarization components of the return beam to a polarization direction of a second of the two polarization components,
wherein the spatial light modulation unit is arranged to modulate phases of the first and second polarization components of the return beam, the first polarization component having been converted by the second conversion unit and the modulation being in the polarization direction corresponding to the polarization direction of the converted first polarization component of the return beam, and
wherein the first conversion unit is arranged to convert the polarization direction of at least one of the first and second polarization components of the return beam once modulated by the light modulation unit to re-create a beam with polarization components with polarization directions that intersect with each other.

6. The adaptive optics apparatus according to claim 1, further comprising:
a polarizing beam splitting unit configured to split light emitted by the light source into two polarization components; and
a polarizing beam combining unit configured to combine the two polarization components.

7. The adaptive optics apparatus according to claim 6,
wherein the first and second conversion units are respectively first and second half-wave plates,
wherein a first compensating plate is disposed between the polarizing beam splitting unit and the light modulation unit, the first compensating plate compensating the first half-wavelength plate for an optical path or a deviation, and
wherein a second compensating plate is disposed between the polarizing beam combining unit and the light modulation unit, the second compensating plate compensating the second half-wavelength plate for an optical path or a deviation.

8. An imaging apparatus for taking an image of an object, the imaging apparatus comprising:
the adaptive optics apparatus according to claim 1; and
an acquiring unit configured to acquire an image of the object on the basis of the return beam returning from the object that is irradiated with light by the irradiation unit.

9. The imaging apparatus according to claim 8, further comprising:
a splitting unit configured to split the light emitted by the light source into a beam that enters the first conversion unit and a reference beam,
wherein the image acquiring unit acquires a tomographic image of the object on the basis of an interference beam that is generated by interference between the return beam and the reference beam, the return beam returning from the object that is irradiated with light by the irradiation unit.

10. An adaptive optics method comprising:
a first conversion step of converting a polarization direction of a first of two different polarization components of light to a polarization direction of a second of the two polarization components;

a spatial light modulation step of modulating the phases of the two polarization components of light, the first polarization component having been converted in the first conversion step and the modulation being in the polarization direction of the converted first polarization component;

a second conversion step of converting the polarization direction of at least one of the first and second polarization components of the light once modulated in the light modulation step to re-create light with polarization directions that intersect with each other; and an irradiation step of irradiating the object with the light that has intersecting polarization directions.

11. An adaptive optics apparatus comprising:

a first conversion unit configured to convert a polarization direction of one of two polarization components of light to a polarization direction of the other of the polarization components, the light being emitted by a light source;

a light modulation unit configured to modulate the two polarization components of light converted by the first conversion unit in the polarization directions that have been converted;

a second conversion unit configured to convert directions of polarization components of the light modulated by the light modulation unit to directions that intersect with each other; and an irradiation unit configured to irradiate an object with the light that is converted by the light modulation unit.

* * * * *